(12) United States Patent
Kwon et al.

(10) Patent No.: US 11,465,962 B2
(45) Date of Patent: Oct. 11, 2022

(54) COMPOSITION FOR DETECTING ACIDIC COMPOUND

(71) Applicants: LG Chem, Ltd., Seoul (KR); Seoul National University R&DB Foundation, Seoul (KR)

(72) Inventors: Won Jong Kwon, Daejeon (KR); Dongwhan Lee, Seoul (KR); Junghwan Kim, Seoul (KR)

(73) Assignees: LG Chem, Ltd.; Seoul National University R&DB Foundation

( * ) Notice: Subject to any disclaimer, the term of this patent is extended or adjusted under 35 U.S.C. 154(b) by 555 days.

(21) Appl. No.: 16/500,152

(22) PCT Filed: Jan. 17, 2019

(86) PCT No.: PCT/KR2019/000714
§ 371 (c)(1),
(2) Date: Oct. 2, 2019

(87) PCT Pub. No.: WO2019/146961
PCT Pub. Date: Aug. 1, 2019

(65) Prior Publication Data
US 2020/0317607 A1    Oct. 8, 2020

(30) Foreign Application Priority Data

Jan. 26, 2018    (KR) .................. 10-2018-0010273

(51) Int. Cl.
| | | |
|---|---|---|
| *C07C 251/70* | (2006.01) | |
| *C07C 251/24* | (2006.01) | |
| *C07C 251/48* | (2006.01) | |
| *C07C 251/86* | (2006.01) | |
| *C07D 401/14* | (2006.01) | |
| *G01N 31/22* | (2006.01) | |

(52) U.S. Cl.
CPC .......... *C07C 251/70* (2013.01); *C07C 251/24* (2013.01); *C07C 251/48* (2013.01); *C07C 251/86* (2013.01); *C07D 401/14* (2013.01); *G01N 31/22* (2013.01)

(58) Field of Classification Search
None
See application file for complete search history.

(56) References Cited

U.S. PATENT DOCUMENTS

| | | | |
|---|---|---|---|
| 5,219,481 A | 6/1993 | Lawson | |
| 8,563,856 B2 | 10/2013 | Herron et al. | |
| 10,556,886 B2 * | 2/2020 | Lee | ............. B01J 20/223 |
| 10,562,845 B2 * | 2/2020 | Lee | ............. C07C 249/16 |
| 2009/0206327 A1 | 8/2009 | Radu et al. | |
| 2011/0186835 A1 | 8/2011 | Herron et al. | |

FOREIGN PATENT DOCUMENTS

| | | | | |
|---|---|---|---|---|
| CN | 102503966 A | 6/2012 | | |
| EP | 3406601 A1 | 11/2018 | | |
| EP | 3406615 A1 | 11/2018 | | |
| JP | H05125032 A | 5/1993 | | |
| KR | 20070104371 A | 10/2007 | | |
| KR | 101272435 B1 | 6/2013 | | |
| KR | 20170080865 A | 7/2017 | | |
| WO | WO-2012121394 A1 * | 9/2012 | ........... | C07C 275/34 |
| WO | WO-2018021882 A1 * | 2/2018 | ............ | B01J 20/223 |
| WO | WO-2018021884 A1 * | 2/2018 | .......... | B01J 31/2243 |

OTHER PUBLICATIONS

E. Asato et al., Chemistry Letters, 678-679 (2000) (Year: 2000).*
S. Sarkar et al., ACS Applied Materials & Interfaces, 6308-6316 (2014) (Year: 2014).*
Asato et al., "First 'Back-to-back' Shaped Compartmental Ligand; Structural Characterization of a Tetranuclear Zinc(II) Complex in a Highly Flattened Form", The Chemical Society of Japan, Chemistry Letters 2000, vol. 29, No. 6, Mar. 2000, pp. 678-679.
International Search Report from Application No. PCT/KR2019/000714 dated Apr. 29, 2019, 2 pages.
Johansson et al., "Functional Tetrametallic Linker Modules for Coordination Polymers and Metal-Organic Frameworks", American Chemical Society, Inorganic Chemistry, vol. 46, No. 6, Nov. 2006, pp. 2224-2236.
Paddock et al., "Chemical CO2 Fixation: Cr(III) Salen Complexes as Highly Efficient Catalysts for the Coupling of CO2 and Epoxides", Journal of American Chemical Society, vol. 123, No. 46, Jun. 2001, pp. 11498-11499.
Sarkar et al., "Redox-Switchable Copper(I) Metallogel: A Metal-Organic Material for Selective and Naked-Eye Sensing of Picric Acid", American Chemical Society, Applied Materials & Interfaces, vol. 6., Apr. 21, 2014, pp. 6308-6316.
Zhang et al., "From Discrete Molecular Cages to a Network of Cages Exhibiting Enhanced CO2 Adsorption Capacity", Angewandte Chemie, A Journal of the German Chemical Society, vol. 129, May 15, 2017, pp. 7895-7899.

(Continued)

*Primary Examiner* — Alexander R Pagano
(74) *Attorney, Agent, or Firm* — Lerner, David, Littenberg, Krumholz & Mentlik, LLP

(57) ABSTRACT

A composition for detecting an acidic compound and a method using the same are discloses herein. In some embodiments, the method includes contacting a composition comprising a metal-organic hybrid structure formed by coordinate bond between a compound represented by the following Chemical Formula 1 or a salt thereof and a metal ion, with an acidic compound to be detected, wherein the composition is in the form of a metallogel prior to contact with the acidic compound, and detecting the acidic compound based on the transition of the composition from the form of a metallogel to a liquid phase. In some embodiments, detection of the acidic compound can be visually confirmed by phase transformation of the composition from a metallogel to a liquid phase.

9 Claims, 6 Drawing Sheets

(56) References Cited

OTHER PUBLICATIONS

Datta et al., A novel chemosensor with visible light excitability for sensing Zn2+ in physiological medium and in HeLa cells. Organic & Biomolecular Chemistry, Jul. 2014, pp. 4975-4982, vol. 12, No. 27.

He et al.,The Synthesis of a Coumarin Carbohydrazide Dinuclear Copper Complex Based Fluorescece Probe and Its Detection Of Thiols, PLoS One, Feb. 2016, e0148026/1-e0148026/12 (12 pages), vol. 11, No. 2.

Li et al., A "turn-on" fluorescent chemosensor for zinc ion with facile synthesis and application in live cell imaging, Analytica Chimica Acta, Mar. 2013, pp. 69-73, vol. 776.

Beck JB, Rowan SJ. Multistimuli, multiresponsive metallo-supramolecular polymers. Journal of the American Chemical Society. Nov. 19, 2003;125(46):13922-3.

Extended European Search Report including Written Opinion for EP19744351.8 dated May 26, 2020; 10 pages.

Zhaofeng Wu, et al., "Multichannel Discriminative Detection of Explosive Vapors with an Array of Nanofibrous Membranes Loaded with Quantum Dots", Sensors (Dec. 31, 2017). 13 pgs.

Search Report from Chinese Application No. 201980002232.1 dated Aug. 3, 2021. 4 pgs.

* cited by examiner

[FIG. 1]
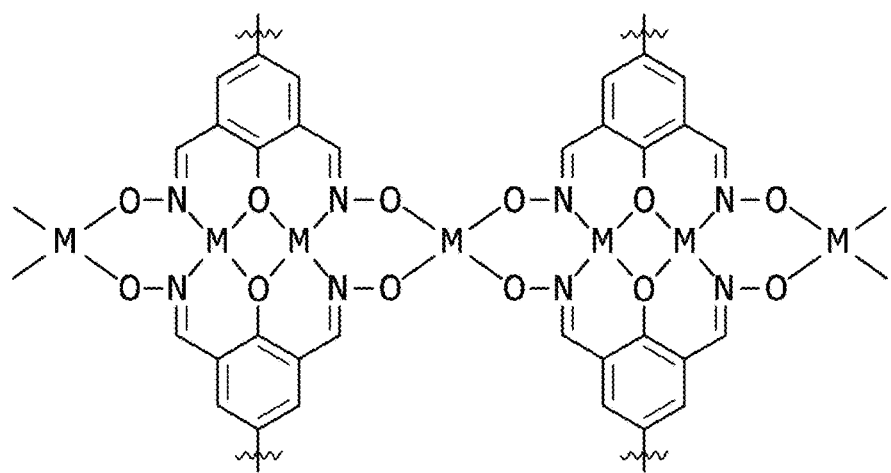
[FIG. 2]
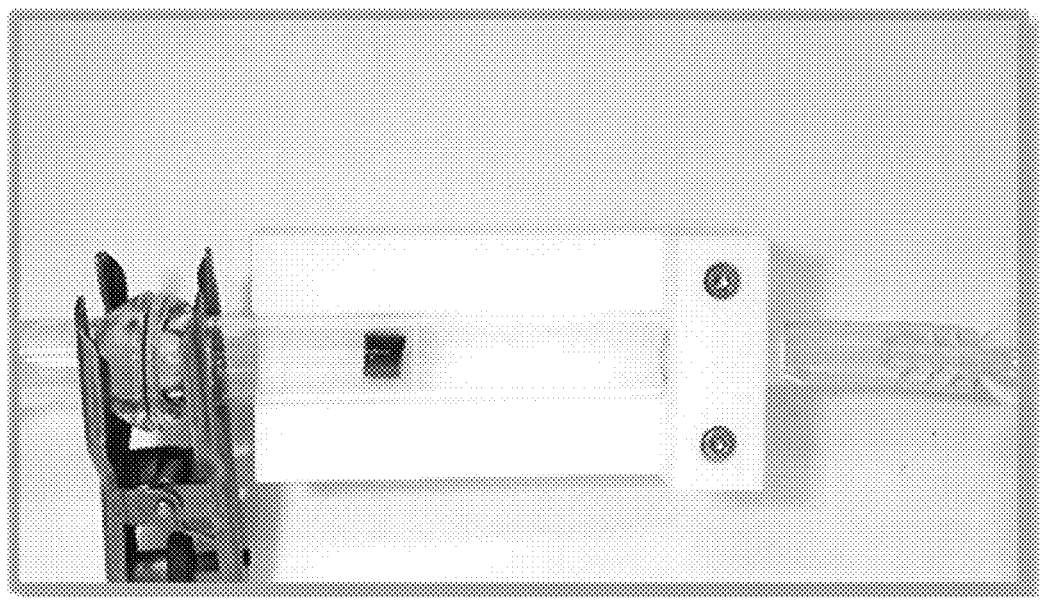

[FIG. 3]
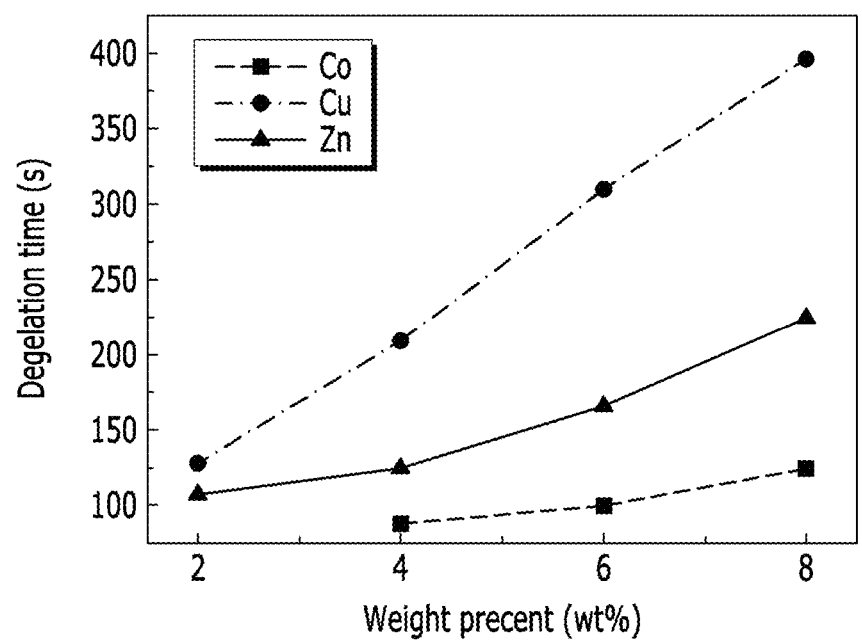

[FIG. 4]
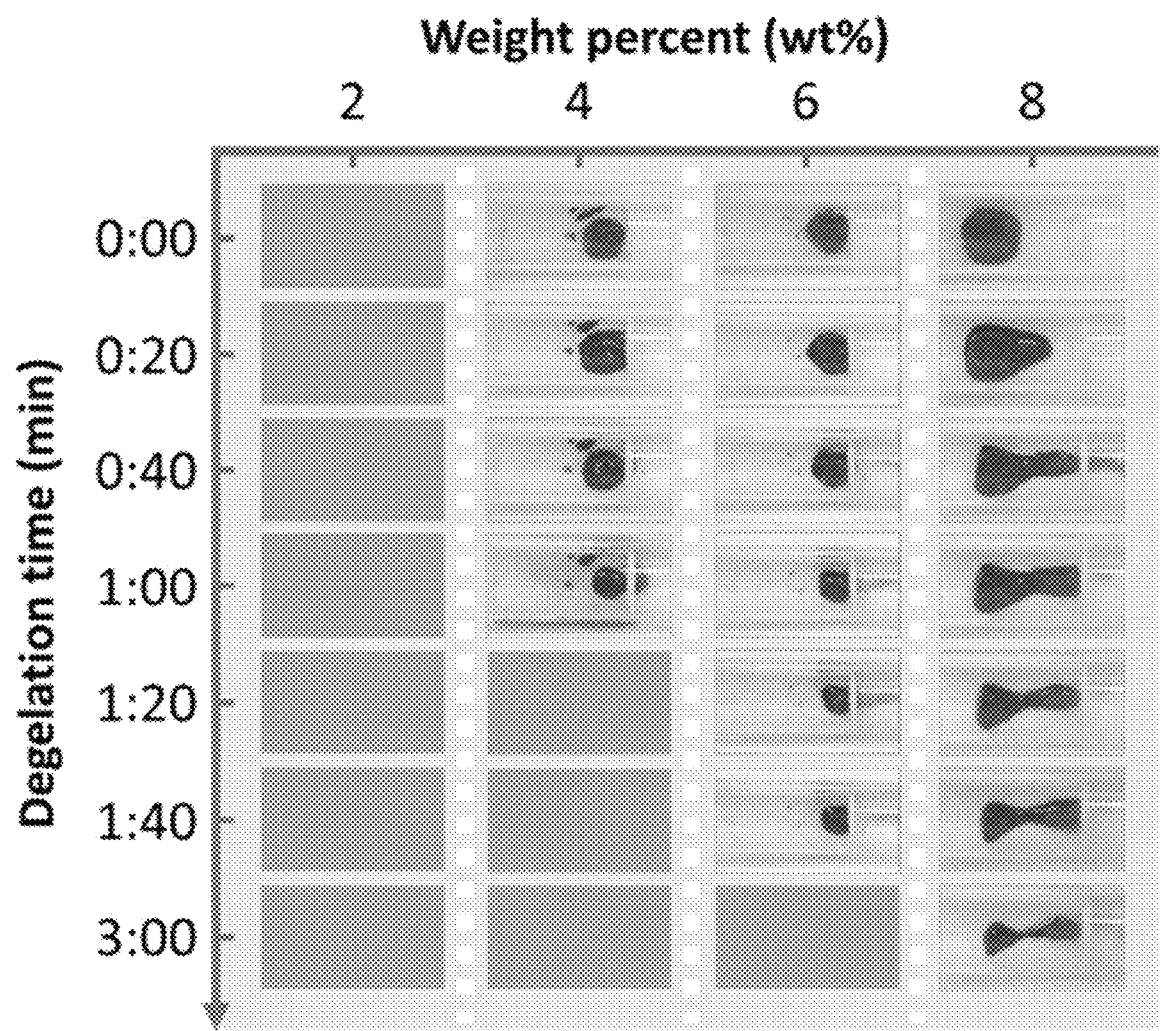

[FIG. 5]
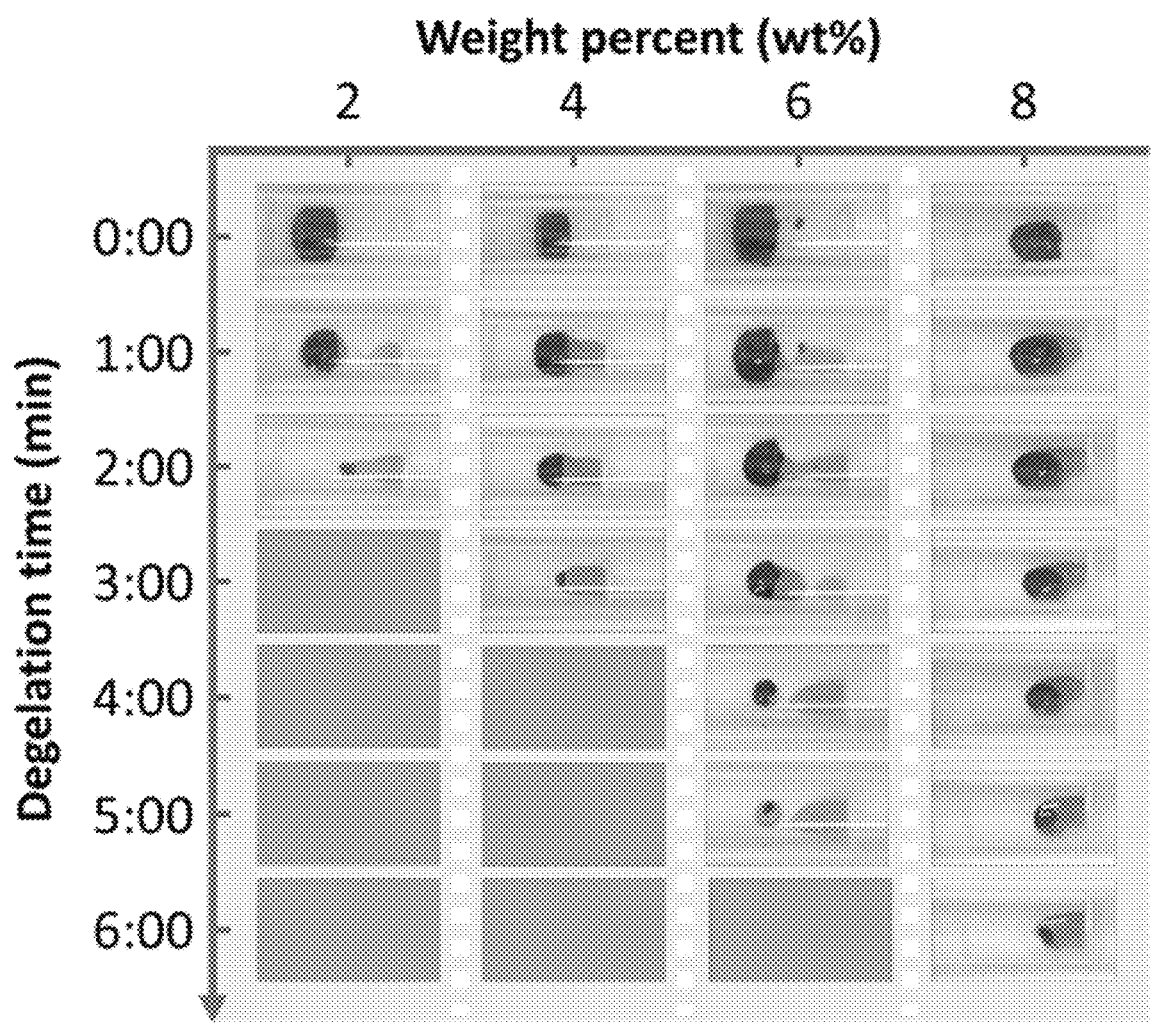

[FIG. 6]
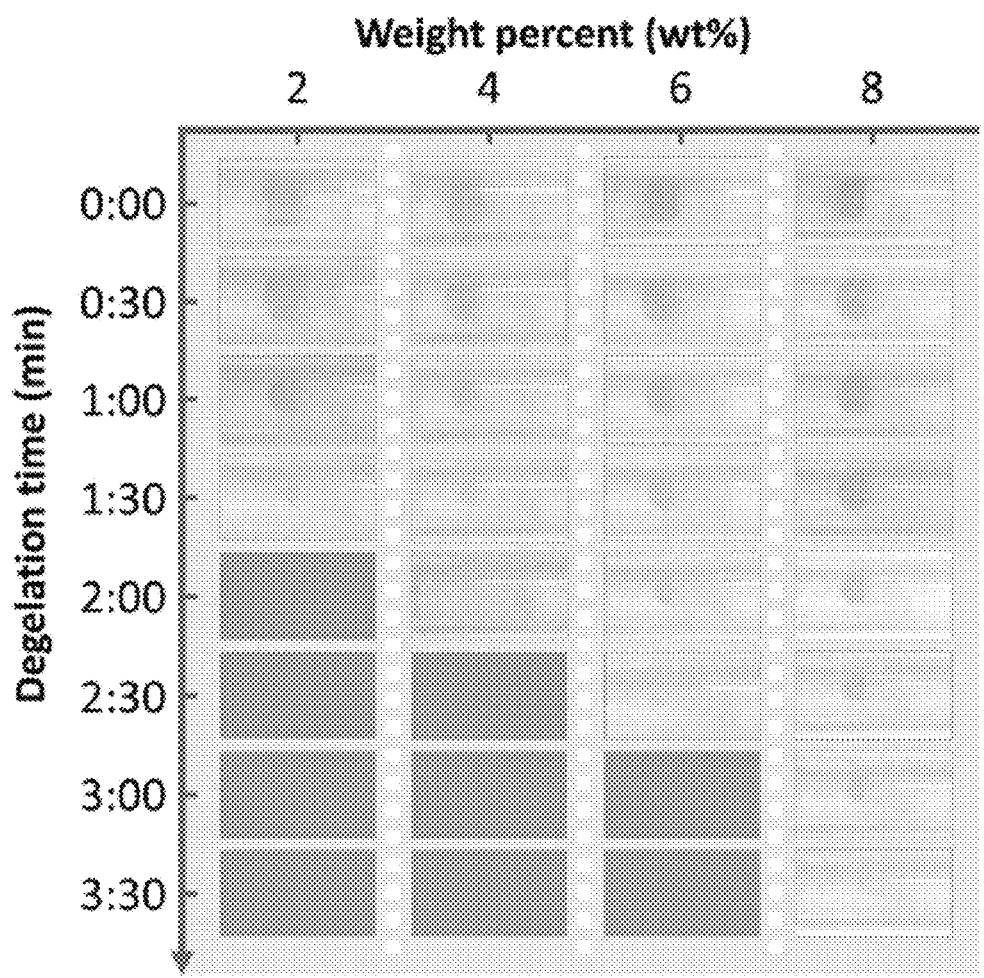

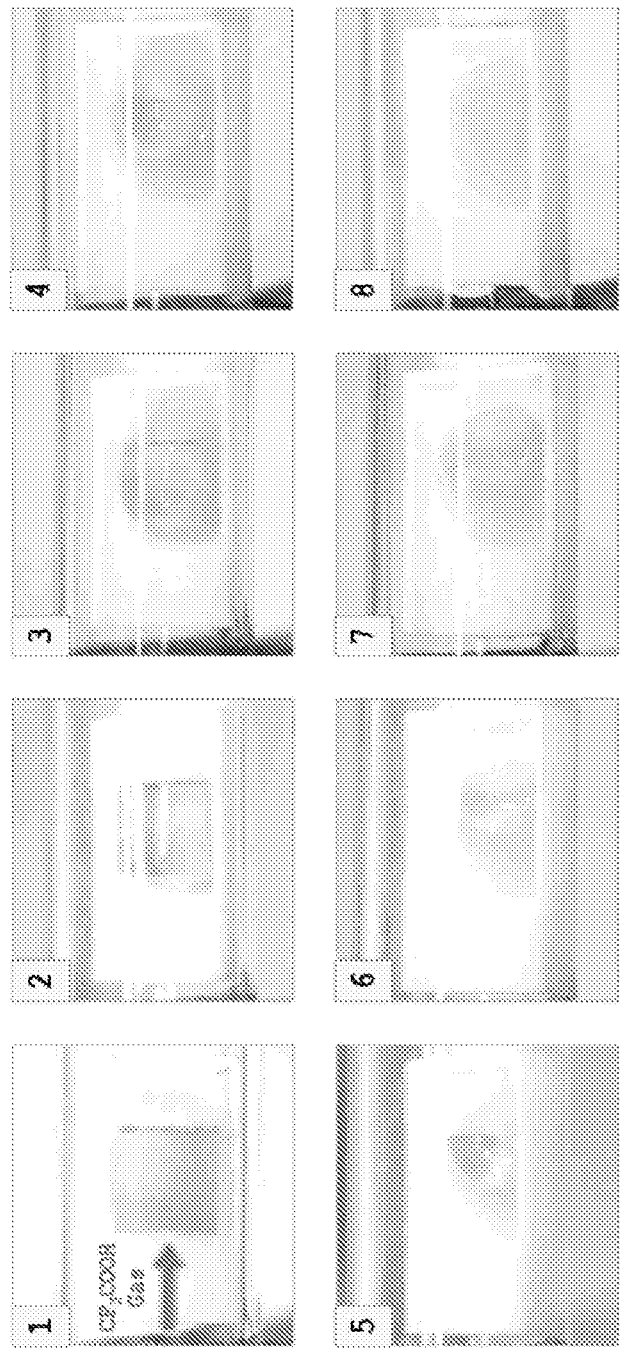
[FIG. 7]

COMPOSITION FOR DETECTING ACIDIC COMPOUND

CROSS-REFERENCE TO RELATED APPLICATION(S)

The present application is a national phase entry under 35 U.S.C. § 371 of International Application No. PCT/KR2019/000714, filed on Jan. 17, 2019, which claims priority from Korean Patent Application No. 10-2018-0010273, filed on Jan. 26, 2018, the entire contents of which are incorporated by reference herein.

TECHNICAL FIELD

The present invention relates to a composition for detecting an acidic compound and a method for detecting an acidic compound using the same.

BACKGROUND ART

Hybrid materials formed by the formation of a network made of metal-organic hybrid structures can simultaneously realize their respective advantages beyond the limitations of organic or inorganic materials consisting of a single material, thereby having new physical properties. In addition, by choosing and combining organic components and inorganic components, the structural diversity of the material and the elaboration of the design can be maximized. Typical industrial applications of such metal-organic hybrid structures include energy storage, biopharmaceuticals, sensors, semiconductor circuit devices, and the like.

Among the metal-organic hybrid structures, metallogel has recently begun to be studied in earnest. Metallogel is produced through a mechanism in which solvent is trapped in the space between substances in a process in which multidentate ligand and metal ion form a polymer or network. Through coordinate bonds between structurally diverse ligands and various metal ions, it is possible to realize structural diversity, which is an advantage of the metal-organic hybrid structures described above. There is also an advantage that a small amount of gelator molecules can be used to produce a large volume of bulk material and to control physical properties.

Metallogel, which is a metal-organic hybrid material, can detect gas molecules using a change in coordination structure, unlike organogel. For example, changes in pH induced by an acidic gas molecule can be detected with a metal gel. When the acidic gas molecules change the pH of the solvent in the gel, the metal dissociates and the network collapses, resulting in a physical change (sol-gel transition) in which the bulk material is changed into solution phase and collapsed. This allows the detection of acidic gas molecules. In addition, detection strategies utilizing oxidation-reduction reactions in which gas molecules coordinate with metal ions and change the oxidation number of the metal have also been actively studied (T. Pal et al., *ACS Appl. Mater. Interfaces* 2014, 6, 6308-6316).

The present inventors have found a reactivity showing sol-gel transition in which metallogel, which is a metal-organic hybrid structure, is sensitive to an acidic compound and thus can be visually easily confirmed. Based on this, the composition and weight percent of various metal-ligand combinations were changed to synthesize a metallogel. It has been found that the sensitivity can be controlled in accordance with the kind and weight percent of the metal by measuring the time during which various kinds of gels change into a liquid phase through the sol-gel transition under acidic gas flow. The present invention has been completed on the basis of such finding.

DETAILED DESCRIPTION OF THE INVENTION

Technical Problem

It is an object of the present invention to provide a composition for detecting an acidic compound and a method for detecting an acidic compound using the same.

Technical Solution

In one aspect of the invention, there is provided a composition for detecting an acidic compound including a metal-organic hybrid structure having a compound represented by the following Chemical Formula 1 or a salt thereof and a metal iron, wherein the compound and the metal ion are coupled via a coordinate bond:

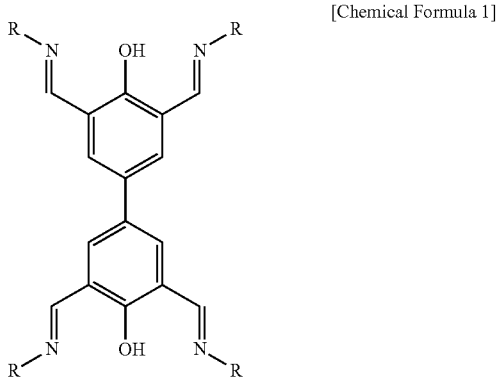

[Chemical Formula 1]

in Chemical Formula 1,
each R is independently —$R_1$, —NH—CO—$R_2$, or —NH—$R_2$,
each $R_1$ is independently —OH, $C_{6-60}$ aryl, $C_{1-10}$ alkyl, or an amino acid residue, and
$R_2$ is $C_{1-10}$ alkyl, $C_{6-60}$ aryl, or $C_{4-60}$ heteroaryl containing any one of N, O, and S.

The compound represented by Chemical Formula 1 has a biphenyl skeleton, and it is capable of charge transfer through π-conjugation. In addition, the compound represented by Chemical Formula 1 has a hydroxy group on each benzene ring, and has two imine groups at the ortho-positions of the hydroxyl group. It can coordinate to metal ions through such hydroxy groups and imine groups.

In particular, the compound represented by Chemical Formula 1 is characterized in that, in addition to the hydroxyl groups and imine groups, the substituent R on the imine group may have an $R_1$ substituent, an amide bond (—NH—CO—$R_2$), or an amine group (—NH—$R_2$) that can additionally coordinate with metal ions. Thus, in addition to the coordinate bonds with metal ions through the hydroxy groups and imine groups, additional coordinate bond with metal ions is possible, and thus, the compound represented by Chemical Formula 1 and metal ions form two-dimensional or three-dimensional network structures.

As an example, the compound of Chemical Formula 1 where R is —OH allows phenoxide and imine group and hydroxy group of oxime moieties to coordinate with a plurality of metals. When a metal salt is added to this compound under basic conditions, a coordination network can be formed in the form of a gel, and the expected network structure is shown in FIG. 1.

The metal-organic hybrid structure is a metallogel and is characterized in that it is converted into a liquid by reacting with an acidic compound, and this process can be confirmed visually and thus can be used for the detection of acidic compounds.

Specifically, the metal-organic hybrid structure exists as a metallogel in which a deprotonated ligand coordinates with a metal under a basic condition to form a network. Thus, this reacts with the acidic compound and the metal ion is dissociated through the protonation of the ligand, resulting in the collapse of the network and conversion to a liquid phase.

The metal of the metal ion is not particularly limited, and for example, may include lanthanide metals such as Tb, Eu, Yb, etc., as well as Period 1 transition metals such as Ti, V, Mn, Fe, Co, Ni, Cu, Zn, etc., Period 2 transition metals such as Zr, Mo, Ru, Rh, Pd, Ag, etc., Period 3 transition metals such as Ir, Pt, Au, etc. In particular, Co, Cu, or Zn is preferable in the aspect of detecting an acidic compound.

In Chemical Formula 1, preferably, $R_1$ is —OH or an amino acid residue.

Preferably, each $R_1$ is independently —OH, phenyl, naphthyl, methyl, ethyl, propyl, isopropyl, butyl, isobutyl, tert-butyl, pentyl, tert-pentyl, neopentyl, isopentyl, sec-pentyl, 3-pentyl, or an amino acid residue selected from the group consisting of alanine, cysteine, aspartic acid, glutamic acid, phenylalanine, histidine, isoleucine, lysine, leucine, methionine, asparagine, pyrrolysine, glutamine, arginine, serine, threonine, selenocysteine, valine, tryptophan, and tyrosine.

The amino acid residue means a structure excluding the amine group in the structure of an amino acid. The amine group condenses with aldehyde to form imine. For example, in the case of alanine, the amino acid residue is propionic acid, which is the structure excluding an amine group in the structure of alanine.

Further, preferably, $R_2$ is methyl, ethyl, propyl, isopropyl, butyl, isobutyl, tert-butyl, pentyl, tert-pentyl, neopentyl, isopentyl, sec-pentyl, 3-pentyl, hexyl, octyl, phenyl, naphthyl, or pyridinyl.

Further, when compound represented by Chemical Formula 1 includes a carboxy group, it may exist in the form of a salt, wherein the counter ion may be $Na^+$, $K^+$, etc.

Representative examples of the compound represented by Chemical Formula 1 are any of compounds represented by the following Chemical Formulas 1-1 to 1-5:

[Chemical Formula 1-1]

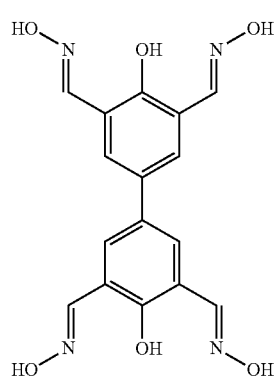

[Chemical Formula 1-2]

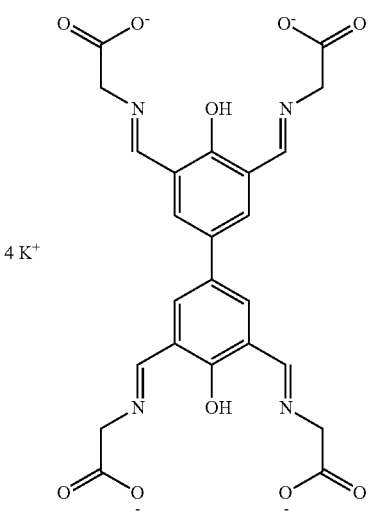

[Chemical Formula 1-3]

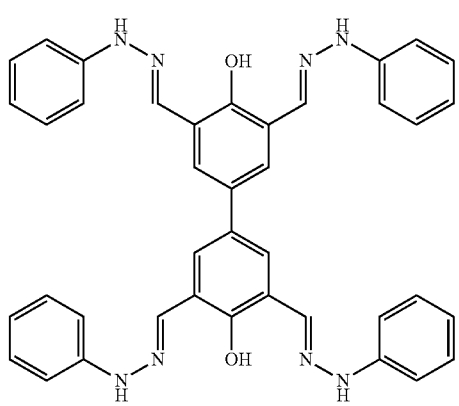

[Chemical Formula 1-4]

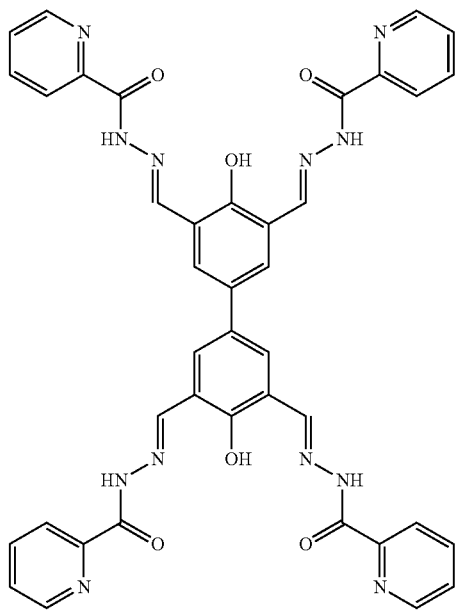

[Chemical Formula 1-5]

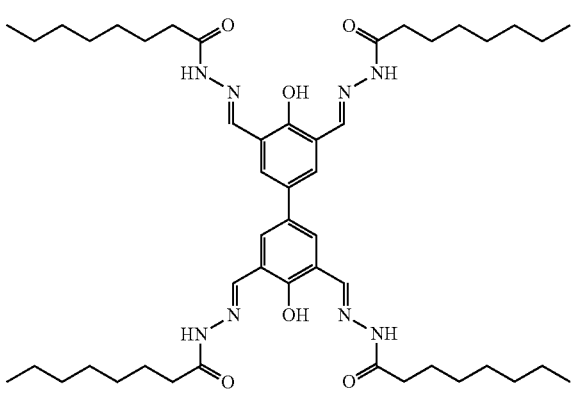

Further, according to another embodiment of the invention, there is provided a method for preparing the above-mentioned compound represented by Chemical Formula 1, as shown in the following Reaction Scheme 1.

[Reaction Scheme 1]

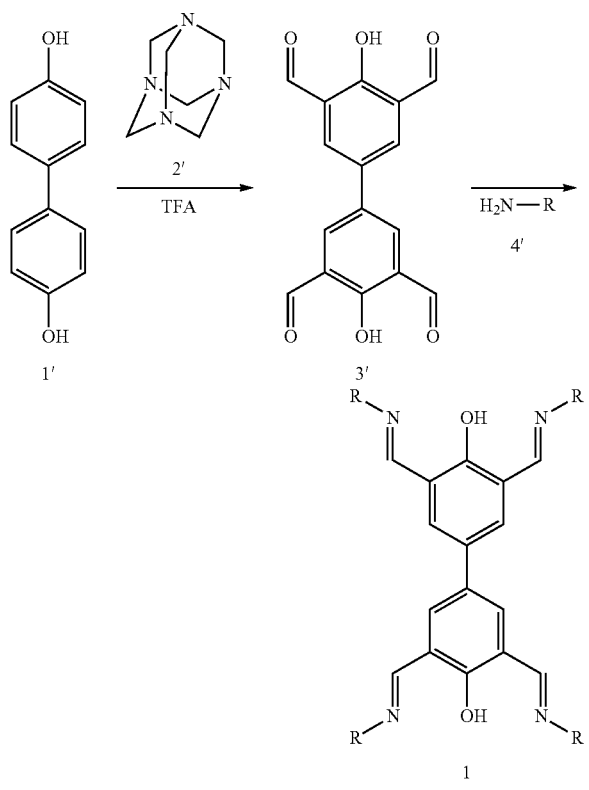

Specifically, the preparation method includes the steps of: reacting a compound represented by Chemical Formula 1', a compound represented by Chemical Formula 2', and trifluoroacetic acid to prepare a compound represented by Chemical Formula 3' (step 1); and reacting the compound represented by Chemical Formula 3' with a compound represented by Chemical Formula 4' (step 2).

Step 1 is a Duff reaction, wherein aldehyde groups are substituted at the ortho-positions to the hydroxy groups of the compound represented by Chemical Formula 1'.

Preferably, the mole ratio of the compound represented by Chemical Formula 1 and the compound represented by the Chemical Formula 2 is 1:20. Further, the trifluoroacetic acid also functions as a solvent, and it is preferably used such that it may dissolve both the compound represented by Chemical Formula 1 and the compound represented by Chemical Formula 2.

Preferably, the reaction temperature of step 1 is 100° C. to 150° C. Further, preferably, the reaction time of step 1 is 1 day to 10 days.

After the reaction of step 1, a step of obtaining the product may be added. As an example, the reaction mixture may be added to an excess amount (1 mole to 5 moles) of hydrochloric acid, and stirred for 1 day to 3 days to obtain a precipitate. For the purification thereof, the precipitate may be recrystallized with dimethylsulfoxide to obtain a compound represented by Chemical Formula 3'.

Step 2 is the reaction of aldehyde and hydroxyamine to form aldoxime, wherein the aldoxime is formed at the aldehyde group of the compound represented by Chemical Formula 3'. In the compound represented by Chemical Formula 4', R is as defined in Chemical Formula 1.

As the solvent of the reaction of step 2, water, a $C_{1-4}$ alcohol, or a mixed solvent thereof may be preferably used, and a water/ethanol mixed solvent or a water/methanol mixed solvent is more preferable.

After the reaction of step 2, a step of obtaining the product may be added. As an example, an excess amount of water may be added to filter the produced precipitate, followed by sequentially washing with water and acetone, thus obtaining a compound represented by Chemical Formula 1.

Further, the metal-organic hybrid structure may be prepared by mixing the above-mentioned compound represented by Chemical Formula 1 and the precursor of the metal.

Preferably, the molar ratio of the compound represented by Chemical Formula 1 to the metal precursor is 1:1 to 1:4, preferably 1:2 (when a metal having a coordination number of 6 is used) or 1:3 (when a metal having a coordination number of 4 is used). Further, the solvent is preferably dimethylsulfoxide or dimethylformamide, and additionally, it is desirable to use one equivalent or more of a base such as triethylamine or sodium methoxide.

Preferably, the above reaction is carried out at 10 to 40° C. Alternatively, sonication treatment or heating at 100° C. to 140° C. for 10 minutes to 10 hours may be added after the reaction.

As described above, the metal-organic hybrid structure is a metallogel and is characterized in that it is converted into a liquid by reacting with an acidic compound, and this process can be confirmed visually and thus can be used for the detection of acidic compounds.

The acidic compound means a compound which induces the transfer of the metal-organic hybrid structure according to the present invention. Preferably, the acidic compound is in liquid or gaseous form, more preferably in gaseous form. In addition, specific examples of the acidic compounds include hydrogen chloride, hydrogen fluoride, hydrogen bromide, trifluoroacetic acid, acetic acid, nitrogen oxide ($NO_x$), nitric acid, sulfur oxide ($SO_x$) or sulfuric acid.

As in Examples described below, it has been found that the metal-organic hybrid structure according to the present invention has changed into a liquid phase when exposed to hydrogen chloride gas, and there was a difference in the rate of change to liquid depending on the weight percentage and the type of metal ions. Thereby, it has been found that not only the possibility of application as an acid gas sensor was confirmed but also the sensitivity of the gas sensor could be improved by controlling the composition of the metal-organic hybrid structure.

Advantageous Effects

As described above, the composition for detecting an acidic compound according to the present invention is characterized in that the detection of the acidic compound can be visually confirmed by utilizing the characteristics of the metal-organic hybrid structure.

BRIEF DESCRIPTION OF DRAWINGS

FIG. 1 schematically shows a network structure of metal-organic frameworks of the present invention.

FIG. 2 shows a state in which the composition for detecting an acidic compound of the present invention is mounted in a cylinder.

FIG. 3 is a graph showing the time (seconds) required for the metal-organic hybrid structure of the present invention to change to a liquid.

FIG. 4 shows a state in which cobalt metallogel changes to a liquid with time by weight percentage in Experimental Example of the present invention.

FIG. 5 shows a state in which copper metallogel changes to a liquid with time by weight percentage in Experimental Example of the present invention.

FIG. 6 shows a state in which zinc metallogel changes to a liquid with time by weight percentage in Experimental Example of the present invention.

FIG. 7 shows the results of expressing the degelation process of zinc metallogel by trifluoroacetic acid in units of time.

DETAILED DESCRIPTION OF THE EMBODIMENTS

Hereinafter, preferred examples will be presented to facilitate understanding of the present invention. However, these examples are provided for a better understanding of the present invention only, and are not intended to limit the scope of the invention.

Preparation Example: Preparation of tetraoxime biphenyl diol

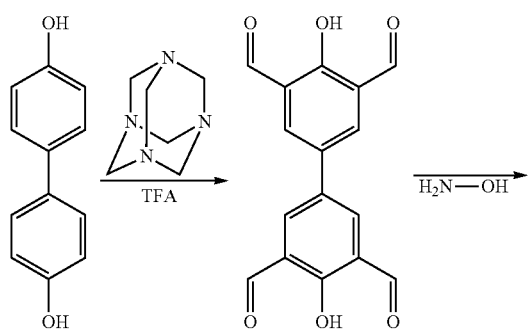

-continued

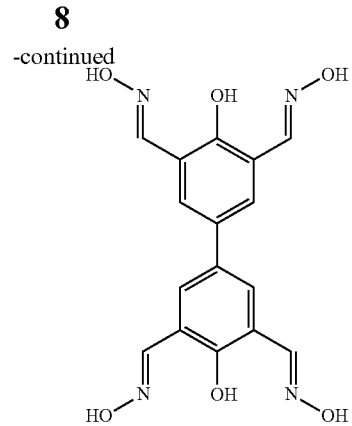

(Step 1)

HMTA (hexamethylenetetramine, 7.530 g, 53.70 mmol) was added into a dried round-bottom flask. The flask was purged with argon, and TFA (trifluoroacetic acid, 50 mL) was added. After completely dissolving HMTA, biphenyl-4,4'-diol (1.000 g, 5.370 mmol) was rapidly added. After confirming that the mixture turned to an orange color, the mixture was heated at 120° C. for 7 days. The product was dark red, and it was poured into 4N HCl (100 mL) to isolate the yellow precipitate. The precipitate was recrystallized with hot DMSO to obtain 2.460 g of yellow microcrystals (yield: 65.1%).

(Step 2)

The compound (0.296 g, 1.000 mmol) prepared in step 1 and $NH_2OH$—HCl (0.420 g, 6.0 mmol) were added into a reactor. After adding water (7 mL), the mixture was heated to 80° C. Methanol was added dropwise until the mixture became transparent. After tightly sealing the reactor, the mixture was heated to 100° C. for 1 hour. After cooling to room temperature, water was added to induce precipitation. The solid material was isolated by filtration, and washed with water to obtain a light yellow product (powder, 0.360 g).

$^1$H NMR (300 MHz, DMSO-d) δ 11.60 (s, 4H), 10.88 (s, 2H), 8.45 (s, 4H), 7.83 (s, s)

Examples 1-1 to 1-4

1) Example 1-1

The compound (tetraoxime biphenol, 25 mg) prepared in the previous Preparation Example was dissolved in DMF (0.88 mL). Then, triethylamine (0.02 mL) was added dropwise and mixed to prepare a solution A. In addition, $Co(OAc)_2 \cdot 4H_2O$ (35 mg) was dissolved in DMF (3.53 mL) to prepare a solution B. The solution A (0.1 mL) and the solution B (0.4 mL) were mixed to prepare a metallogel, which was then sonicated for 1 minute to increase the strength of the metallogel. The metallogel thus prepared was named "Cobalt metallogel 2 wt %".

2) Examples 1-2 to 1-4

A metallogel was prepared in the same manner as in Example 1-1, except that the amount of DMF used was controlled as shown in Table 1 below during the preparation of the solutions A and B,

TABLE 1

|  |  | Amount of DMF used during preparation of solution A | Amount of DMF used during preparation of solution B |
|---|---|---|---|
| Example 1-1 | Cobalt metallogel 2 wt % | 0.88 mL | 3.53 mL |
| Example 1-2 | Cobalt metallogel 4 wt % | 0.43 mL | 1.73 mL |
| Example 1-3 | Cobalt metallogel 6 wt % | 0.28 mL | 1.13 mL |
| Example 1-4 | Cobalt metallogel 8 wt % | 0.21 mL | 0.83 mL |

Examples 2-1 to 2-4

1) Example 2-1

The compound (tetraoxime biphenol, 25 mg) prepared in the previous Preparation Example was dissolved in DMF (1.09 mL). Then, triethylamine (0.02 mL) was added dropwise and mixed to prepare a solution A. In addition, Cu(acac)$_2$ (55 mg) was dissolved in DMF (4.36 mL) to prepare a solution B. The solution A (0.1 mL) and the solution B (0.4 mL) were mixed to prepare a metallogel, which was then sonicated for 1 minute to increase the strength of the metallogel. The metallogel thus prepared was named "Cobalt metallogel 2 wt %".

2) Examples 2-2 to 2-4

A metallogel was prepared in the same manner as in Example 2-1, except that the amount of DMF used was controlled as shown in Table 2 below during the preparation of the solutions A and B,

TABLE 2

|  |  | Amount of DMF used during preparation of solution A | Amount of DMF used during preparation of solution B |
|---|---|---|---|
| Example 2-1 | Copper metallogel 2 wt % | 1.09 mL | 4.36 mL |
| Example 2-2 | Copper metallogel 4 wt % | 0.53 mL | 2.14 mL |
| Example 2-3 | Copper metallogel 6 wt % | 0.35 mL | 1.39 mL |
| Example 2-4 | Copper metallogel 8 wt % | 0.26 mL | 1.02 mL |

Examples 3-1 to 3-4

1) Example 3-1

The compound (tetraoxime biphenol, 25 mg) prepared in the previous Preparation Example was dissolved in DMF (1.04 mL). Then, triethylamine (0.02 mL) was added dropwise and mixed to prepare a solution A. In addition, Zn(acac)$_2$·H$_2$O (50 mg) was dissolved in DMF (4.15 mL) to prepare a solution B. The solution A (0.1 mL) and the solution B (0.4 mL) were mixed to prepare a metallogel, which was then sonicated for 1 minute to increase the strength of the metallogel. The metallogel thus prepared was named "Zinc metallogel 2 wt %".

2) Examples 3-2 to 3-4

A metallogel was prepared in the same manner as in Example 3-1, except that the amount of DMF used was controlled as shown in Table 3 below during the preparation of the solutions A and B,

TABLE 3

|  |  | Amount of DMF used during preparation of solution A | Amount of DMF used during preparation of solution B |
|---|---|---|---|
| Example 3-1 | Zinc metallogel 2 wt % | 1.04 mL | 4.15 mL |
| Example 3-2 | Zinc metallogel 4 wt % | 0.51 mL | 2.03 mL |
| Example 3-3 | Zinc metallogel 6 wt % | 0.33 mL | 1.33 mL |
| Example 3-4 | Zinc metallogel 8 wt % | 0.24 mL | 0.98 mL |

Experimental Example

As shown in FIG. 2, a fixed volume of the metallogel of Examples previously prepared was placed inside the cylinder. After an o-ring was attached and the system was isolated from the outside by using a clamp, hydrogen chloride gas was flowed into the cylinder at a constant flow rate and flow rate. Then, the time (second) was measured while observing the degelation state of metallogel. The time required for complete degelation of metallogel is shown in Table 4 below. This graph (FIG. 3) and the image observed based on a fixed time interval are shown in FIGS. 4 to 6.

TABLE 4

|  | 2 wt % | 4 wt % | 6 wt % | 8 wt % |
|---|---|---|---|---|
| Copper metallogel | 128 s | 210 s | 310 s | 397 s |
| Cobalt metallogel | — | 88 s | 100 s | 124 s |
| Zinc metallogel | 107 s | 125 s | 166 s | 225 s |

As described above, it was confirmed that hydrogen chloride gas could be detected within a short time, and the metallogel exhibited a time difference according to the metal and weight % thereof. Therefore, it can be confirmed that the above-mentioned characteristics can be used to control the detection of the acidic compound and its sensitivity.

Experimental Example 2

As shown in FIG. 2, 4 wt % of Zinc metallogel (1.2 mL) of Example 3-2 previously prepared was placed inside the cylinder. An o-ring was attached to one end of the cylinder and connected to an oil bubbler to check the internal pressure of the cylinder. The other end of the cylinder was connected with a round bottom flask containing trifluoroacetic acid and a tygon tube. Nitrogen was poured into a round bottom flask so that the trifluoroacetic acid vapor passed through the cylinder, and the degelation process of metallogel was recorded by digital imaging and captured at a fixed time interval (20 seconds) and shown in FIG. 7.

The invention claimed is:
1. A method of detecting an acidic compound, comprising:
  contacting a composition comprising a metal-organic hybrid structure formed by coordinate bond between a compound represented by the following Chemical Formula 1 or a salt thereof and a metal ion, with an acidic compound to be detected, wherein the composition is in the form of a metallogel prior to contact with the acidic compound; and detecting the acidic compound based on the transition of the composition from the form of a metallogel to a liquid phase:

[Chemical Formula 1]

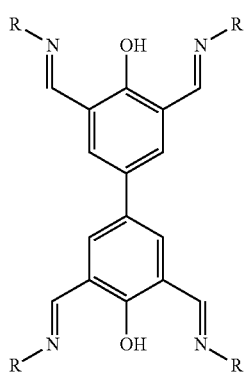

in Chemical Formula 1, each R is independently -$R_1$, —NH—CO-$R_2$, or —NH-$R_2$, each $R_1$ is independently —OH, $C_{6-60}$ aryl, $C_{1-10}$ alkyl, or an amino acid residue, and $R_2$ is $C_{1-10}$ alkyl, $C_{6-60}$ aryl, or $C_{4-60}$ heteroaryl containing any one of N, O, and S.

2. The method according to claim 1, wherein each $R_1$ is independently —OH, phenyl, naphthyl, methyl, ethyl, propyl, isopropyl, butyl, isobutyl, tert-butyl, pentyl, tert-pentyl, neopentyl, isopentyl, sec-pentyl, 3-pentyl, or an amino acid residue selected from the group consisting of alanine, cysteine, aspartic acid, glutamic acid, phenylalanine, histidine, isoleucine, lysine, leucine, methionine, asparagine, pyrrolysine, glutamine, arginine, serine, threonine, selenocysteine, valine, tryptophan, and tyrosine.

3. The method according to claim 1, wherein $R_2$ is methyl, ethyl, propyl, isopropyl, butyl, isobutyl, tert-butyl, pentyl, tert-pentyl, neopentyl, isopentyl, sec-pentyl, 3-pentyl, hexyl, octyl, phenyl, naphthyl, or pyridinyl.

4. The method according to claim 1, wherein the compound represented by Chemical Formula 1 are compounds represented by the following Chemical Formulas 1-1 to 1-5:

[Chemical Formula 1-1]

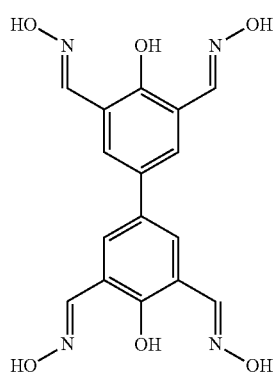

[Chemical Formula 1-2]

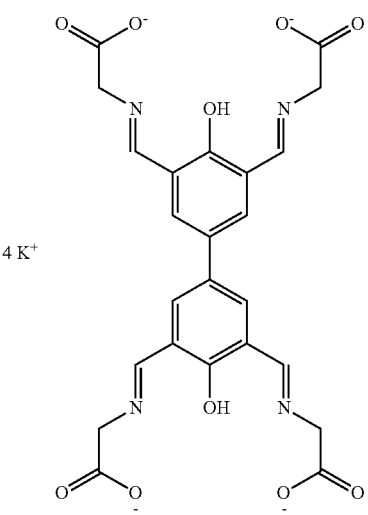

4 $K^+$

[Chemical Formula 1-3]

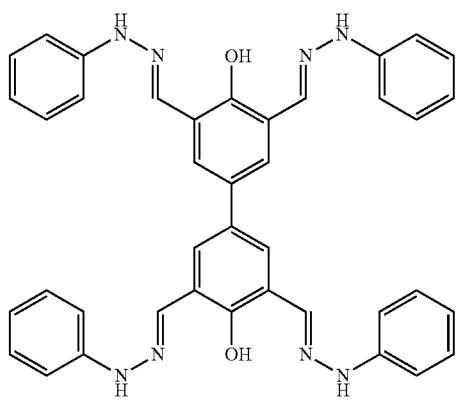

[Chemical Formula 1-4]

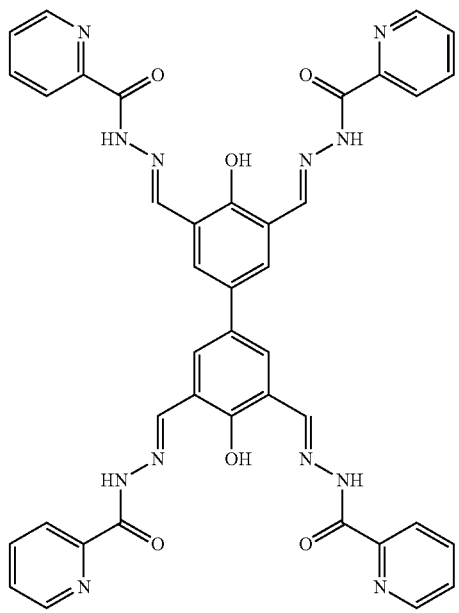

-continued

[Chemical Formula 1-5]

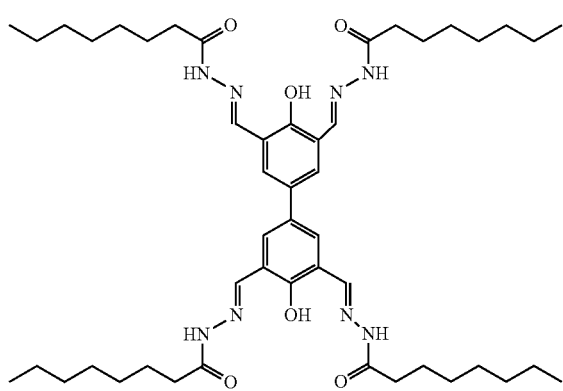

5. The method according to claim 1, wherein the metal of the metal ion is Period 1 transition metal, Period 2 transition metal, Period 3 transition metal, or lanthanide metal.

6. The method according to claim 1, wherein the metal of the metal ion is Ti, V, Mn, Fe, Co, Ni, Cu, Zn, Zr, Mo, Ru, Rh, Pd, Ag, Ir, Pt, Au, Tb, Eu, or Yb.

7. The method according to claim 1, wherein the acidic compound is a liquid or a gas.

8. The method according to claim 1, wherein the acidic compound is hydrogen chloride, hydrogen fluoride, hydrogen bromide, trifluoroacetic acid, acetic acid, nitrogen oxide, nitric acid, sulfur oxide or sulfuric acid.

9. The method according to claim 1, wherein the composition further comprises:
   a solvent, wherein the solvent is trapped between spaces in the metal-organic hybrid structure.

* * * * *